United States Patent
Zamore

[11] Patent Number: 5,900,444
[45] Date of Patent: May 4, 1999

[54] IRRADIATION CONVERSION OF THERMOPLASTIC TO THERMOSET POLYURETHANE

[76] Inventor: Alan Zamore, 23 Mountain Ave., Monsey, N.Y. 10952

[21] Appl. No.: 08/727,145

[22] Filed: Oct. 8, 1996

[51] Int. Cl.⁶ .................................. C08J 3/28; C08F 8/30; C08F 8/00; C08L 75/04
[52] U.S. Cl. ........................ 522/137; 522/90; 522/95; 522/96; 522/135; 522/136; 522/138; 522/139; 522/140; 522/173; 522/174; 525/123; 525/127; 525/131; 525/452; 525/455; 528/75
[58] Field of Search ........................ 522/90, 95, 96, 522/138, 137–139, 140, 135, 136, 173, 174; 525/123, 127, 131, 452, 455; 528/75

[56] References Cited

U.S. PATENT DOCUMENTS

| | | | |
|---|---|---|---|
| 3,616,364 | 10/1971 | D'Alelio | 525/123 |
| 3,642,964 | 2/1972 | Rausch, Jr. et al. | 264/40 |
| 3,674,743 | 7/1972 | Verdol et al. | 528/68 |
| 3,871,908 | 3/1975 | Spoor et al. | 525/440 |
| 4,255,552 | 3/1981 | Schollenberger et al. | 528/50 |
| 4,289,682 | 9/1981 | Peters | 525/440 |
| 4,331,697 | 5/1982 | Kudo et al. | 427/2 |
| 4,342,793 | 8/1982 | Skinner et al. | 427/44 |
| 4,358,354 | 11/1982 | Iida | 522/96 |
| 4,443,588 | 4/1984 | Fukuda et al. | 528/75 |
| 4,552,815 | 11/1985 | Dreher et al. | 428/415 |
| 4,567,083 | 1/1986 | Arioka et al. | 428/141 |
| 4,607,084 | 8/1986 | Morris | 525/454 |
| 4,762,884 | 8/1988 | Goyert et al. | 525/28 |
| 4,820,782 | 4/1989 | Ueno | 525/454 |
| 4,897,433 | 1/1990 | Sugo et al. | 522/116 |
| 4,948,859 | 8/1990 | Echols et al. | 528/28 |
| 5,084,529 | 1/1992 | Crano | 525/455 |
| 5,109,097 | 4/1992 | Klun et al. | 528/75 |
| 5,116,652 | 5/1992 | Alzner | 428/36.9 |
| 5,236,978 | 8/1993 | Selvig et al. | 524/81 |
| 5,266,669 | 11/1993 | Onwunaka et al. | 528/28 |
| 5,284,883 | 2/1994 | Ueno et al. | 522/79 |
| 5,328,940 | 7/1994 | Zimmer | 522/31 |
| 5,336,585 | 8/1994 | Takahashi et al. | 522/96 |
| 5,374,704 | 12/1994 | Muller et al. | 528/66 |
| 5,382,633 | 1/1995 | Scott et al. | 525/279 |
| 5,438,106 | 8/1995 | Siranovich et al. | 525/440 |

FOREIGN PATENT DOCUMENTS 901410   5/1972   Canada.

OTHER PUBLICATIONS

"Radiation Crosslinked Thermoplastic Polyurethane", published in the journal *International Polymer Science and Technology*, vol. 19, No. 1, pp. T/6–T/9 (1992).

*Primary Examiner*—Rabon Sergent
*Attorney, Agent, or Firm*—Dale Lynn Carlson; Wiggin & Dana

[57] ABSTRACT

Disclosed is a radiation-crosslinkable thermoplastic polyurethane composition comprising (a) the reaction product of: (i) an aliphatic polyisocyanate, and (ii) a polyahl, and (b) a reactive monomer cross-linker. The reactive monomer cross-linker facilitates cross-linking of the reaction product upon contact of the cross-linker-containing composition with photons from a radiation source. Also disclosed is a process for converting this thermoplastic polyurethane into a thermoset polyurethane by irradiating the thermoplastic polyurethane with a beam of photons.

20 Claims, No Drawings

5,900,444

IRRADIATION CONVERSION OF THERMOPLASTIC TO THERMOSET POLYURETHANE

FIELD OF THE INVENTION

This invention relates generally to the conversion of thermoplastic polyurethanes into thermoset polyurethanes and more specifically to such thermoset polyurethanes exhibiting improved physical and chemical properties, relative to the corresponding thermoplastic polyurethanes. The thermoset polyurethanes are advantageously prepared using aliphatic diisocyanates and an reactive monomer crosslinker.

BACKGROUND OF THE INVENTION

Thermoplastic polyurethanes are relatively easy to process into a wide variety of fabricated products. Unfortunately, however, the high temperature stability of these polyurethanes, as well as their stability in some commonly-used organic solvents, are less than might be desired. Accordingly, methodology has been developed to provide heat-induced crosslinking to convert thermoplastic polyurethanes into thermoset polyurethanes having the desired stability at high temperatures and in the presence of solvents. By way of illustration, U.S. Pat. No. 4,255,552 discloses thermoset polyurethane elastomers obtained by adding organic peroxides to a liquid polyurethane-forming composition prior to reacting the composition to form the polyurethane. The '552 patent teaches that the liquid polyurethane-forming composition containing "unactivated hydrogen peroxide" may be formed into a desired article and then heated to thermoset the article, or provided in solid form such as sheet, crumbs, or granules which are then formed into a desired article that is then thermoset by heating the article. The organic peroxides disclosed in the '552 patent are said to have a half-life of greater than one hour at 100° C. Unfortunately, these peroxide-containing compositions are less stable than might be desired during melt processing or thermoforming of the polyurethane composition into the desired finished article, thus providing technology that is not commercially practical.

As an alternative to heat induced crosslinking of thermoplastic polyurethanes, their conversion into thermoset polyurethanes by irradiation is known in the art. A technical journal article entitled "Radiation Crosslinked Thermoplastic Polyurethane", published in the journal *International Polymer Science and Technology*, Vol. 19, No. 1, pp. T/6–T/9 (1992), discloses the production of such thermoset polyurethanes using a polyisocyanate and methacrylate monomer as a radiation-cross-linkable monomer. This technical journal article does not disclose the particular polyisocyanate used in making polyurethanes disclosed therein. Unfortunately, methacrylate is more heat sensitive than otherwise might be desired, causing a risk of premature cross-linking during storage or shipping and prior to the desired conversion of the thermoplastic polyurethane into a thermoset polyurethane. Further, not all polyisocyanates perform alike in irradiation-crosslinking of TPUs. Indeed, the present inventor has been unsuccessful in attempts to cross-link TPU formulations based upon aromatic polyisocyanates to provide a desirable article. Instead of cross-linking, the resulting article exhibits an undesirable discoloration.

In view of the above, there is a continuing need in the polyurethanes manufacturing community for a polyurethane-forming composition that is readily thermoset by cross-linking when desired, but is also less sensitive to unwanted heat-induced cross-linking during storage and prior to use than prior art polyurethane-forming compositions, most notably prior art peroxide, acrylate, and methacrylate-containing compositions. Such a composition desirably would provide advantageous processing capability, such as by extrusion, when the composition is in the thermoplastic state, and advantageous elevated temperature stability and solvent resistance when the composition is thermoset after formation into the desired product. The present invention provides one such desirable composition, together with processes for the production of the composition.

SUMMARY OF THE INVENTION

In one aspect, the present invention relates to a radiation-crosslinkable thermoplastic polyurethane composition comprising:
(a) the reaction product of:
    (i) an aliphatic polyisocyanate, and
    (ii) a polyahl, and
(b) a reactive monomer cross-linker to provide cross-linking of said reaction product upon contacting said cross-linker with ionizing photons from a radiation source.

In another aspect, the present invention relates to a radiation-crosslinkable thermoplastic polyurethane composition comprising:
(a) a mixture of:
    (i) an aliphatic polyisocyanate, and
    (ii) a polyahl, and
(b) a reactive monomer cross-linker to provide cross-linking of said reaction product upon contacting said cross-linker with ionizing photons from a radiation source.

In still another aspect, the present invention relates to a process for converting a thermoplastic polyurethane to a thermoset polyurethane. The process comprises the steps of:
(a) preparing a liquid or solid thermoplastic polyurethane composition comprising a reactive monomer cross-linker and a reaction product of:
    (i) an aliphatic polyisocyanate, and
    (ii) a polyahl, and
(b) irradiating said composition with a beam of photons in order to cause said reactive monomer cross-linker in said composition to cross-link at least a portion of said reaction product, thereby converting said composition into said thermoset polyurethane.

In yet another aspect, the present invention relates to a process for converting a thermoplastic polyurethane to a thermoset polyurethane comprising the steps of:
(a) preparing a liquid or solid thermoplastic polyurethane-forming composition comprising a reactive monomer cross-linker and also comprising:
    (i) an aliphatic polyisocyanate, and
    (ii) a polyahl, and
(b) reacting said aliphatic polyisocyanate with said polyahl to form a polyurethane composition containing said cross-linker, and
(c) irradiating said polyurethane composition with a beam of photons in order to cause said reactive monomer cross-linker in said composition to cross-link at least a portion of said reaction product, thereby converting said composition into said thermoset polyurethane.

In still another aspect, the present invention relates to a process for converting a thermoplastic polyurethane to a thermoset polyurethane. The process comprises the steps of:

(a) preparing a liquid or solid thermoplastic polyurethane composition comprising the reaction product of:
(i) an aliphatic polyisocyanate, and
(ii) a polyahl, and
(b) irradiating said composition with a beam of photons in order to cause cross-linking of at least a portion of said reaction product, thereby converting said composition into the thermoset polyurethane.

In another aspect, the present invention relates to the thermoset polyurethane products produced by the above-recited processes.

In yet another aspect, the present invention relates to a process for producing a thermoset product which comprises irradiating a thermoplastic elastomer composition containing a reactive monomer cross-linker in order to cross-link said thermoplastic elastomer to convert the thermoplastic elastomer to said thermoset product.

These and other aspects will become apparent upon reading the following detailed description of the invention.

DETAILED DESCRIPTION OF THE INVENTION

It has now been surprisingly found, in accordance with the present invention, that a thermoplastic polyurethane (so-called "TPU") or polyurea is suitably converted to a thermoset polyurethane or polyurea by employing a polyurethane-forming or preformed polyurethane (or a polyurea-forming or preformed polyurea) composition comprising an aliphatic diisocyanate and a polyahl, or the reaction product thereof, and employing a select reactive monomer (preferably an allylic monomer, more preferably an allylic monomer that is essentially free of peroxide, acrylate and methacrylate moieties) as a crosslinking promoter during subsequent irradiation of the polyurethane-forming or the polyurethane composition. Irradiating the composition causes the polyurethane to convert from a thermoplastic state to a thermoset state without encountering the risk of premature cross-linking that has plagued the above-discussed prior art compositions. The resulting thermoset polyurethane exhibits advantageous physical and chemical properties. For example, the thermoset polyurethane is preferably essentially free of discoloration often associated with prior art thermoset polyurethanes made from TPUs. The term "essentially free of discoloration", as used herein, is intended to mean that the thermoset polyurethane of the present invention advantageously exhibits essentially none of the undesirable yellow, brown or orange discoloration that typically characterizes thermoset resins produced in accordance with the aforementioned prior art patents.

Irradiating the composition to convert the thermoplastic polyurethane to a thermoset polyurethane is suitably effected using a beam of photons, preferably from a source of high energy ionizing photons, in order to cause cross-linking of the thermoplastic polyurethane composition to occur. The radiation source suitably provides the desired irradiation of the thermoplastic polyurethane. As used herein, the term "irradiation", in the context of the photon beam employed in the present invention, is used expansively to encompass bombardment of the target thermoplastic polyurethane with photons, e.g. beta (also referred to herein as e-beam) particles, gamma particles, ultraviolet ("uv") radiation, combinations thereof, and the like, in order to effect conversion of the TPU to the desired thermoset polyurethane. Although the energy output from the radiation source to the thermoplastic polyurethane composition can vary over a wide range, it is preferred that, when using e-beam irradiation, an amount of radiation of from about 1 and about 100 Mega Rads, more preferably between 10 and 50 Mega Rads, most preferably between 10 and 20 Mega Rads, be imparted to the composition over a suitable period of time to insure that the polyurethane being irradiated does not overheat.

As used herein, the term "thermoplastic" is used in its broad sense to designate a material that is reprocessable at an elevated temperature, whereas "thermoset" designates a material that exhibits high temperature stability without such reprocessability at elevated temperatures. The term "thermoplastic elastomer" designates a material that possesses an elastic, rubber-like property such that it exhibits at least a one hundred percent elongation without breaking when stretched at room temperature, and will return to its unstretched length when released.

As used herein, the term "allylic monomer" is intended to designate a cross-linking moiety for polyurethanes that is monomeric and contains an allyl group. Preferably, the allylic monomer is free of peroxide, acrylate, and methacrylate moieties.

Particularly useful reactive monomers include, for example, triallyisocyanurate (also referred to herein as "TAIC"), triallylcyanurate (also referred to herein as "TAC"), diallyl phthalate (also referred to herein as "DAP"), and meta-phenylene dimaleimide (also referred to herein as MPDM), and combinations thereof. The TAIC is commercially available as a liquid dispersion, and, alternatively, on a silicate substrate (75% TAIC on 25% silicate) as SYNPRO PLC-4185, a product of Synpron Corporation. Although less desired, other useful reactive monomers include methacrylate-containing monomers, such as trimethyolpropane trimethacrylate (TMPTMA), commercially available as Sartomer's SR-350.

The reactive monomer is suitably admixed with the polyurethane-forming composition prior to preparation of the TPU, or admixed with the TPU prior to preparation of the desired thermoset polyurethane product.

Although not wishing to be bound by any particular theory, it is believed that the essentially discoloration-free appearance of the thermoset polyurethanes produced in accordance with the present invention is attributable to the use of an aliphatic polyisocyanate in the polyurethane-forming compositions employed in the present invention. The present inventor has found that the irradiation employed in the present invention does not significantly discolor the aliphatic polyisocyanate-based polyurethane compositions employed in this invention. In contrast, such irradiation appears to severely discolor comparison polyurethane compositions based upon aromatic polyisocyanates. Further, the present inventor has found that aliphatic polyisocyanate-based TPUs are suitably converted to thermoset compositions by irradiation, whereas the benzene molecules in backbone of aromatic polyisocyanate-based TPU's seem to absorb high energy radiation (e-beam or gamma rays), thus rendering aromatic isocyanate-based TPU's stable (and, hence, not easily thermoset) in the presence of irradiation. Moreover, although aromatic polyisocyanate-based TPU's typically exhibit better chemical properties, such as resistance to organic solvents and oils, than prior art aliphatic polyisocyanate-based TPU, the compositions of the present invention overcome this disadvantage since the thermoset polyurethanes of the present invention exhibit excellent physical and chemical properties.

The aliphatic polyisocyanate useful as a reactant in forming the polyurethanes employed in the present invention is preferably selected from commercially-available aliphatic polyisocyanates such as, for example, 1,6-hexamethylene diisocyanate ("HDI"), isophorone diisocyanate ("IPDI"), ethylene diisocyanate, 1,4-tetramethylene diisocyanate, 2,2, 4-trimethyl-1,6-hexamethylene diisocyanate, 1,10-decanemethylene diisocyanate, 1,12-dodecanemethylene diisocyanate, cyclohexane-1,3-diisocyanate, cyclohexane-1, 4-diisocyanate, 1-isocyanato-2-isocyanatomethyl cyclopentane, isophorone diisocyanate, bis-(4-isocyanatocyclohexyl)-methane, 1,3- and/or 1,4-bis-(isocyanatomethyl)-cyclohexane, bis-(4-isocyanato-3-methyl-cyclohexyl)-methane, 1-isocyanato-1-methyl-4(3)-isocyanatomethyl cyclohexane, 4,4'-dicyclohexylmethane diisocyanate, and combinations thereof.

The "polyahl" useful as a reactant in forming the polyurethanes employed in the present invention is an active hydrogen-containing compound that is reactive with the aliphatic polyisocyanate to produce the desired polyurethane. In addition, the term polyahl is intended to encompass compounds that react in situ to generate an active hydrogen-containing moiety such as imines. An active hydrogen group is a group which has a hydrogen atom which, because of its position in the molecule, displays activity according to the Zerewitnoff test described by Woller in the Journal of American Chemical Society, Vol. 49, page 3181 (1927). Illustrative of such active hydrogen groups are —OH, —NH—, —COOH, —SH and —CONH—. Particularly suitably polyahls include polyols, imines (such as ketimines and aldimines), oxazolidines, and combinations thereof, preferably having a weight average molecular weight of between about 100 and about 10,000, more preferably between about 100 and about 5,000, most preferably between about 200 and about 2,000.

Suitable amines are aliphatic or cycloaliphatic, primary or secondary amines. Preferred amines are poly(alkyleneoxy) alkylamines.

Suitable polyols include polyether polyols and polyester polyols. The preferred polyols useful in the present invention have a hydroxyl functionality of no greater than about 2, more preferably less than 1.5, advantageously about 1, in order to prevent the formation of very high molecular weight polyurethane prepolymers which result in coating viscosities higher than desired for ready application. The polyether polyols are prepared by polymerization of alkylene oxides with water, polyhydric alcohols with two to eight hydroxyl groups, or amines. Polyester polyols are suitably prepared by a condensation reaction of a polycarboxylic acid with a polyhydric alcohol.

In preparing the polyurethanes useful in the present invention, the ratio of NCO equivalents in the polyisocyanate to the OH equivalents in the active hydrogen-containing compound can vary over a wide range of between about 10:1 and about 1:10, preferably between about 2:1 and about 1:2.

Catalysts are typically employed in the polyurethane-forming reaction. Useful catalysts include those which facilitate the reaction of the polyahl with the aliphatic polyisocyanate reactants. Suitable catalysts are the organotin catalysts, alone or in combination with amine catalysts, particularly tertiary amine catalysts. Illustrative organotin catalysts include dibutyltin dilaurate, stannous octoate, and combinations thereof. Illustrative amine catalysts include the following:

N,N'-dimethylethanolamine,
N,N-dimethylamino-ethoxyethanol,
N,N'-dimethylaminoethyl-N-methylethanolamine,
N,N-dimethyl-N',N'-2-hydroxypropyl-1,3-propylene diamine, N,N,N'-trimethyl-N'-hydroxyethyl-bis(amino ethyl) ether, N,N-bis(3-dimethylaminopropyl) amino-2-propanol, and combinations thereof. The catalysts are suitably employed in the polyurethane-forming formulation in a total amount of between about 0.01% and about 5%, preferably between about 0.01% and about 1%, by weight based upon the weight of the polyurethane-forming composition.

In preparing the desired polyurethane, the polyether polyol(s), polyisocyanate(s), chain extender(s) such as polyether or polyester glycol chain extenders, and other desired components are reacted, typically at an elevated temperature. One method of forming the desired thermoplastic polyurethane is by continuous processing utilizing an extruder, as illustrated by the disclosures of U.S. Pat. No. 3,642,964, incorporated herein by reference in its entirety. An alternative method involves batch processing, followed by grinding and extrusion of the formed elastomer as is well-known in the art. Although either the prepolymer method or the one-shot method can be used, the one-shot method is preferred. The one-shot method is intended to also include the process whereby the diisocyanate has been converted to a quasi-prepolymer by reaction with a minor amount (i.e., less than about 10 percent on an equivalent basis) of polyol prior to carrying out the polyurethane forming reaction.

In preparing the desired polyurethane, urethane forming catalysts can be used, as discussed above, as well as the usual compounding ingredients such as antioxidants or other antidegradants. Typical antioxidants include hindered phenols, butylated hydroxytoluene ("BHT"), and the like. Other optional compounding ingredients include, for example, plasticizers, adhesion promoters, fillers and pigments like clay, silica, fumed silica, carbon black, talc, phthalocyanine blue or green, $TiO_2$, U-V absorbers, $MgCO_3$, $CaCO_3$ and the like. The compounding ingredients are suitably employed in an amount of between 0 and about 75 weight percent based upon the weight of the elastomer. The polymerization reaction may be carried out in a single reaction (one-shot process), or in one or more sequential steps (prepolymer process), using either bulk polymerization or solution polymerization. When solution polymerization is used, polar solvents such as tetrahydrofuran ("THF"), dimethylformamide ("DMF"), and dimethylacetamide ("DMAC") are typically utilized. In the one-shot process, all the isocyanate-reactive components are reacted simultaneously with the polyisocyanate. In such process, it is normal practice to blend all components except the polyisocyanate into a "B-side" mixture, which is then reacted with the polyisocyanate to form the polyurethane and/or polyurea elastomer. However, the order of mixing is not critical as long as the components do not undesirably react before all components are present. The reaction mixture is then suitably placed in a mold, or extruded through an extruder, and cured at a suitable temperature. The apparatus used for blending and molding is not especially critical. Hand mixing, conventional machine mixing, and the so-called reaction injection molding (RIM) equipment are all suitable. In the prepolymer process, all or a portion of one or more of the isocyanate reactive materials is reacted with a stoichiometric excess of the polyisocyanate to form an isocyanate-terminated prepolymer. This prepolymer is then allowed to react with the remaining isocyanate-reactive materials to prepare the polyurethane and/or polyurea elastomer. The prepolymer can be prepared with either the polyether or the chain extender, or a mixture of both.

The mixing of the reactants can be carried out at ambient temperature (typically from 20° C. to 25° C.) and the resulting mixture is then heated to a temperature of the order of about 40° C. to about 130° C., preferably to a temperature of about 90° C. to about 120° C. Alternatively, and preferably, one or more of the reactants is preheated to a temperature within the above ranges before the admixing is carried out. Advantageously, in a batch procedure, the heated reaction components are subjected to degassing in order to remove entrained bubbles of air, water, or other gases before the reaction takes place. This degassing is accomplished conveniently by reducing the pressure under which the components are maintained until no further evolution of bubbles occurs. The degassed reaction components are then admixed and transferred to suitable molds or extrusion equipment or the like and cured at a temperature of the order of about 20° C. to about 115° C. The time required for curing will vary the temperature of curing and also with the nature of the particular composition, as is known in the art.

The polyurethanes produced in accordance with the present invention are useful in a variety of applications, including sealants, elastomers, coatings, adhesives, and in the fabrication of a wide variety of household, commercial, and industrial products. For example, the present invention is suitably employed to produce a crosslinked polyurethane that is a medical catheter product. This crosslinked polyurethane product retains its flexural modulus at body temperatures longer than catheters made from prior art TPU's. As another illustration, the present invention is suitably employed to produce flexible wire and cable jackets having improved temperature and fluid resistance, as compared analogous products made from prior art TPU's. Other illustrative uses for the thermoset polyurethanes produced in accordance with the present invention include the following: orthdontic ligatures which last longer than those made from prior art TPU's; seals, gaskets and o-rings which are easier to fabricate than those made from prior art cast polyurethanes and exhibiting better temperature stability, compression set and fluid resistance than those made from prior art TPU's; sneaker and shoe soles that are longer wearing than those made from prior art TPU's; longer lasting toner wiper blades for copiers and laser printers, as compared to those made from prior art TPU's; and, medical implanted devices and wires which last longer inside body parts and cavities than those made from prior art TPU's.

The polyurethane employed in the present invention is suitably shaped into the desired product configuration while in the thermoplastic state, and then irradiated to thermoset the polyurethane product. The TPU can be in solid form, such as pellets, prior to forming the desired polyurethane product. Alternatively, solid TPU can be dissolved in organic solvent, and used for dipping, spraying or otherwise coating the dissolved TPU onto a substrate, and then the coating is thermoset by irradiation.

As used herein, the term "molecular weight" is intended to designate number average molecular weight. All percents used herein are percents by weight unless otherwise specified. As used herein, the term "phr" denotes "parts by weight per hundred parts of resin".

The following Example is intended to illustrate, but in no way limit the scope of, the present invention.

EXAMPLE 1

Part A—Preparation and Testing of a Thermoset Polyurethane of the Present Invention A sample of dried aliphatic polyester, thermoplastic polyurethane resin, having a hardness of 80 Shore A and a melt index of 2 at 165° C., was compounded with 4 phr of SYNPRO PLC-4185 (75% TAIC on 25% silicate) allylic monomer to yield a mixture containing 3 phr TAIC. This mixture was compression molded at 125° C. for 10 minutes to yield a 6"×6"×0.070" plaque. The plaque was exposed to 14 Mega Rads of high energy electron beam irradiation in order to convert the plaque to a thermoset plaque.

After irradiation the thermoset plaque was tested for various physical properties in accordance with ASTM tests as identified in Table 1 below. The test results are provided in Table 1.

TABLE 1

| Physical Properties | 14 MRads |
| --- | --- |
| Ultimate elongation at break (%) | 425 |
| 200% Modulus (psi) | 900 |
| Compression set (%) | 58.5 (72 hours at 100° C.) |
| Color change (visual) | minimal |

| Fluid Resistance Fluid | Temp | 14 MRads Time | Observation |
| --- | --- | --- | --- |
| Mil-L-16884 | 121° C. | 2.5 hrs | swell + 13%, brown stained, somewhat tacky |
| Tetrahydrofuron | 20° C. | 2.5 hrs | swelled, very friable, did not dissolve** |
| 100% IPA* | 20° C. | 2.5 hrs | no change |
| 50% IPA* | 20° C. | 2.5 hrs | no change |
| Water, distilled | 20° C. | 2.5 hrs | no change |

*IPA = isopropyl alcohol
**unirradiated pellets completely dissolved

Part B—Temperature Stability Test

The irradiated polyurethane of Part A above did not melt or flow at elevated temperatures as demonstrated by probing the irradiated plaque with an electrically heated solder iron tip at a temperature of approximately 300° C.

Part C—Comparison with Aromatic Polyisocyanate-based Polyurethanes

Dow's PELLETHANE 55D aromatic polyisocyanate-based polyurethane resin was compounded with 3 phr TAIC allylic monomer, and exposed to 15 Mrads of high energy electron beam irradiation. No crosslinking was observed based upon the results of a hot iron test (described hereinabove) on this composition, and the physical properties were unchanged relative to the unirradiated neat pellets. Instead, the irradiated material discolored by turning dark brown.

In a second experiment, Dow's PELLETHANE 55D aromatic polyisocyanate-based polyurethane resin Pellethane 55D was compounded with 3 phr of TMPTMA (an acrylic monomer) and exposed to 15 Mrads of high energy electron beam irradiation. No crosslinking was observed in the hot iron test as described above, and the physical properties were unchanged relative to the unirradiated neat pellets. The irradiated material turned dark brown.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A radiation-cross-linkable thermoplastic polyurethane composition that is solid at room temperature comprising:
   (a) a reaction product of:
      (i) an aliphatic polyisocyanate, and
      (ii) a polyahl, and
   (b) an allylic monomer cross-linker or meta-phenylene dimaleimide to provide conversion of said reaction product from a thermoplastic to a thermoset state upon contacting said cross-linker or meta-phenylene dimaleimide with photons from a radiation source.

2. The composition of claim 1 wherein said allylic monomer cross-linker is free of peroxide, acrylate and methacrylate moieties.

3. The composition of claim 1 wherein said allylic monomer cross-linker or meta-phenylene dimaleimide is selected from the group consisting of triallylisocyanurate, triallylcyanurate, diallyl phthalate, meta-phenylene dimaleimide, and combinations thereof.

4. The composition of claim 1 wherein said aliphatic polyisocyanate is selected from the group consisting of 1,6-hexamethylene diisocyanate ("HDI"), isophorone diisocyanate ("IPDI"), ethylene diisocyanate, 1,4-tetramethylene diisocyanate, 2,2,4-trimethyl-1,6-hexamethylene diisocyanate, 1,10-decanemethylene diisocyanate, 1,12-dodecanemethylene diisocyanate, cyclohexane-1,3-diisocyanate, cyclohexane-1,4-diisocyanate, 1-isocyanato-2-isocyanatomethyl cyclopentane, 1,3- and/or 1, 4-bis-(isocyanatomethyl)-cyclohexane, bis-(4-isocyanato-3-methyl-cyclohexyl)-methane, 1-isocyanato-1-methyl-4(3)-isocyanatomethyl cyclohexane, 4,4'-dicyclohexylmethane diisocyanate, and combinations thereof.

5. A process for converting a thermoplastic polyurethane that is solid at room temperature to a thermoset polyurethane comprising the steps of:
(a) preparing a thermoplastic polyurethane composition comprising an allylic monomer cross-linker or meta-phenylene dimaleimide and a reaction product of:
(i) an aliphatic polyisocyanate, and
(ii) a polyahl, and
(b) irradiating said composition with a beam of photons in order to cause said monomer cross-linker or meta-phenylene dimaleimide in said composition to convert said composition into said thermoset polyurethane.

6. The process of claim 5 wherein said allylic monomer cross-linker is free of peroxide, acrylate and methacrylate moieties.

7. The process of claim 5 wherein said beam of photons comprises radiation selected from the group consisting of beta particles, gamma particles, ultraviolet radiation, and combinations thereof.

8. The process of claim 5 wherein said beam of photons imparts between about 1 and about 100 Mega Rads of energy to said composition.

9. The process of claim 5 wherein said beam of photons is provided in the form of electron beam radiation.

10. The process of claim 5 which comprises the additional step of dissolving said thermoplastic polyurethane composition in an organic solvent between step (a) and step (b) of claim 5.

11. The process of claim 10 wherein said beam of photons comprises radiation selected from the group consisting of beta particles, gamma particles, ultraviolet radiation, and combinations thereof.

12. The process of claim 10 wherein said beam of photons imparts between about 1 and about 100 Mega Rads of energy to said composition.

13. A process for converting a thermoplastic polyurethane that is solid at room temperature to a thermoset polyurethane comprising the steps of:
(a) preparing a thermoplastic polyurethane-forming composition comprising an allylic monomer cross-linker or meta-phenylene dimaleimide and also comprising:
(i) an aliphatic polyisocyanate, and
(ii) a polyahl, and
(b) reacting said aliphatic polyisocyanate with said polyahl to form a thermoplastic polyurethane composition containing said cross-linker, and
(c) irradiating said thermoplastic polyurethane composition with a beam of photons in order to cause said composition to convert into said thermoset polyurethane.

14. The process of claim 13 wherein said allylic monomer cross-linker is free of peroxide, acrylate and methacrylate moieties.

15. The process of claim 13 wherein said allylic monomer cross-linker or meta-phenylene dimaleimide is selected from the group consisting of triallylisocyanurate, triallylcyanurate, diallyl phthalate, meta-phenylene dimaleimide, and combinations thereof.

16. The process of claim 13 wherein said beam of photons comprises radiation selected from the group consisting of beta particles, gamma particles, ultraviolet radiation, and combinations thereof.

17. The process of claim 13 wherein said beam of photons imparts between about 1 and about 100 Mega Rads of energy to said composition.

18. The thermoset polyurethane produced by the process of claim 5.

19. The thermoset polyurethane produced by the process of claim 10.

20. The thermoset polyurethane produced by the process of claim 13.

* * * * *